United States Patent [19]

Prince et al.

[11] Patent Number: 4,800,078

[45] Date of Patent: Jan. 24, 1989

[54] IMMUNOTHERAPEUTIC METHOD OF TREATING RESPIRATORY DISEASE BY INTRANASAL ADMINISTRATION OF IGB

[75] Inventors: Gregory Prince; Robert Chanock, both of Bethesda; Val G. Hemming, Gaithersburg, all of Md.

[73] Assignee: The United States of America as represented by the Secretary of the Department of Health and Human Services, Washington, D.C.

[21] Appl. No.: 55,008

[22] Filed: May 28, 1987

[51] Int. Cl.[4] .................. A61K 39/42; A61K 39/395
[52] U.S. Cl. ...................................... 424/86; 424/85.8
[58] Field of Search ............... 530/387; 514/956, 957, 514/958, 997; 424/86, 85

[56] References Cited

U.S. PATENT DOCUMENTS 4,192,860  3/1980  Griffiths ................................ 424/43
4,512,972  4/1985  Schmidt-Ruppin .................. 424/89
4,659,563  4/1987  Dobkin ................................ 530/387

FOREIGN PATENT DOCUMENTS 1030408  7/1983  U.S.S.R. ................................ 424/86

OTHER PUBLICATIONS

Prince et al., *J. Virology*, 55:517–520, 1985.
Hemming et al., *J. Infectious Dis.*, 152:1083–1087, 1985.
Prince et al., *Virus Research*, 3:193–206, 1985.
Prince et al., *Pediatric Infectious Disease*, 5:S201–S203, 1986.
*Annals of the New York Academ of Science*, vol. 443:67–68, 1985, Edited by Norman S. Braveman et al.
Rabin et al., *Pav. J. Biol. Sci.*, 1986, vol. 21, No. 2.

Primary Examiner—Howard E. Schain
Assistant Examiner—Jeff Kushan
Attorney, Agent, or Firm—Holman & Stern

[57] ABSTRACT

A new immunotherapeutic method of treating lower respiratory tract infection caused by respiratory syncytial virus (RSV) is disclosed. The method employs topical application of RSV antibodies into the lower respiratory tract. The new treatment modality is more effective and rapid than the conventional therapy.

1 Claim, No Drawings

IMMUNOTHERAPEUTIC METHOD OF TREATING RESPIRATORY DISEASE BY INTRANASAL ADMINISTRATION OF IGB

BACKGROUND OF THE INVENTION

1. Technical Field

The present invention is related to immunotherapy of respiratory disease caused by respiratory syncytial virus (RSV) or other respiratory viruses. More particularly, the present invention is related to a more effective and rapid method of treating lower respiratory tract disease caused by RSV by direct administration of neutralizing antibodies into the lower respiratory tract.

2. State of the Art

Lower respiratory tract infection caused by RSV is a serious problem in infants and children, particularly infants under six months of age. Currently licensed therapy for RSV requires the delivery of ribavirin (1-beta-D-ribofuranosyl-1,2,4,-triazole-3-carboxamide) by small particle aerosol for 12-20 hours a day for at least 3 days (Hall et al, 1983 *New Eng. J. Med.* 308: 1443–1447; Taber et al, 1983 *Pediatrics* 72: 613–618). A more effective and quick acting treatment of the respiratory disease caused by RSV is, therefore, an obvious need.

SUMMARY OF THE INVENTION

It is, therefore, an object of the present invention to provide a more efficacious, simpler and quick acting method of treating virus-caused respiratory disease than the currently available therapeutic modalities.

Other objects and advantages will become evident from the Detailed Description of the Invention.

DETAILED DESCRIPTION OF THE INVENTION

The above and various other objects and advantages of the present invention are achieved by a method of treating respiratory disease, comprising topically administering to a host susceptible to or suffering from infection by respiratory syncytial virus (RSV), an effective amount of neutralizing antibodies to produce prophylactic or therapeutic effect against virus infection.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

MATERIALS AND METHODS

Animals

Cotton rats (*Sigmodon hispidus*) and owl monkeys were obtained from the Veterinary Resources Branch, Division of Research Services, National Institues of Health. A small nucleus colony of cotton rats, maintained behind a germ-free barrier for the past 10 years, provided animals for the production colony. Adult cotton rats were immunized with inactivated Sendai virus vaccine (Microbiological Associates) at least 3 weeks before study. *Sigmodon fulviventer* were obtained from the same source, initiated from wild-trapped animals.

IVIG Administration

A single lot of purified human IVIG (Sandoglobulin, lot #2.370.069.0) was used for all experiments. This lot had a RSV neutralizing antibody titer of 1:2905. Cotton rats infected three days earlier by intranasal instillation of A2 strain of RSV ($10^4$ pfu/animal) were anesthetized with methoxyflurane and inoculated intraperitoneally (IP) or intranasally (IN) with a varying dose of IVIG. The volume of IVIG inoculated IN was 0.1 ml/100 gm body weight. Intranasal administration of IVIG to fully anesthetized cotton rats or monkeys resulted in rapid delivery of the inoculum into the lungs.

Virus Assay

Cotton rats were sacrificed by carbon dioxide asphyxiation 24 hours after administration of IVIG. Lungs and nasal tissues (including nasal turbinates) were homogenized in 10 parts (w/v) of Hanks' balanced salt solution supplemented with 0.218M sucrose, 4.4 mM glutamate, 3.8 mM $KH_2PO_4$ and 3.2 mM $K_2HPO_4$, and the resulting suspension was stored at $-70$ degrees C. until assayed. Virus titer was determined by plaque assay on HEp-2 cell monolayers as described by Prince et al (1978) *Am. J. Pathol.* 93: 771–792, and was expressed in plaque-forming units (pfu)/gm tissue.

Viral assay in owl monkeys was similarly conducted using tracheal lavage from the animals.

Antibody and Immunoglobulin Assays

Neutralizing antibody was measured by a plaque-reduction neutralization assay as described by Prince et al, supra, using a 60% plaque-reduction endpoint. Human IgG in cotton rat serum was measured by radial immunodiffusion (Meloy Laboratories, Springfield, Va.) and low levels (<10 mg/dl) were confirmed by standard competitive inhibition ELISA such as described by Boswirth et al, 1983, *J. Immunol. Methods* 62: 331–336.

Histology

Lungs were removed from the thorax and inflated through the trachea with neutral buffered formalin. Histologic sections were stained with hematoxylin and eosin.

Comparison of therapeutic efficacy of IVIG administered parenterally (IP) or topically (IN)

Administration of IVIG by the IP route, in a dose of 2 gm/kg or more, 3 days after infection of the respiratory tract with RSV, reduced the titer of RSV in the lungs $10^{-2}$ or more within 24 hours. As a consequence virus could not be detected on the fourth day post-infection in pulmonary tissue of 80–90% of animals treated in this manner (Table 1). A significant reduction in the quantity of virus in the nose was also observed, but this effect was not as dramatic as that observed in the lungs.

IVIG administered by the intranasal route is more effective than IVIG inoculated parenterally. Thus, topically administered IVIG cleared pulmonary RSV in every animal when a dose of 0.05 gm/kg or greater was used. However, IVIG administered in this way had no effect on the quantity of RSV present in the nose (Table 1). The therapeutic effect of IN IVIG on pulmonary viral titer diminished with decreasing dose and the minimum effective does was observed to be 0.00625 gm/kg ($p<0.001$). Cotton rats inoculated topically with the largest dose of IVIG (0.1 gm/kg), attained near peak levels of this material in serum within 5 hours, but RSV antibodies did not reach a concentration which allowed their detection by the neutralization assay. The concentration of IVIG in serum 24 hours after topical administration ranged from 61 to 140 $\mu$g/ml for cotton rats which received 0.025 to 0.05 gm/Kg body weight, a dose which cleared or substantially (almost completely) cleared pulmonary RSV. The concentration of IVIG in the serum of cotton rats which exhibited a similar therapeutic effect when IVIG was administered parenterally (4 to 8 gm/Kg body weight) was 120 to 202 times higher, i.e., 12,379 to 16,829 µg/ml (Table 1).

TABLE 1

Therapeutic Effect of Human IVIG Administered Intraperitoneally (IP) or Intranasally (IN) Three Days Post Infection

| Route IVIG administered 3 days post-infection ($10^{4.0}$ pfu RSV) | Dose IVIG (gm/kg body weight) | # of animals | Level in serum one day following IVIG treatment | | Viral titer 4 days post-infection, $\log_{10}$ pfu/gm geometric mean ± S.E. (% of animals free of detectable virus) | |
|---|---|---|---|---|---|---|
| | | | Titer of RSV neutralizing antibodies (reciprocal) | IVIG (µg/ml) | Lungs | Nose |
| Control | — | 24 | <20 | 0 | 4.26 ± 0.08 (0) | 4.80 ± 0.17 (0) |
| I.P. | 8.0 | 13 | 692 | 16,829 | 2.15 ± 0.10$^a$ (85) | 2.82 ± 0.36$^a$ (62) |
| | 4.0 | 10 | 518 | 12,379 | 2.04 ± 0.05$^a$ (90) | 3.57 ± 0.36$^b$ (10) |
| | 2.0 | 10 | 302 | 4,769 | 2.26 ± 0.19$^a$ (80) | 3.61 ± 0.44$^b$ (20) |
| | 1.0 | 8 | 142 | 3,760 | 3.27 ± 0.27$^a$ (13) | 4.85 ± 0.14$^c$ (0) |
| | 0.25 | 4 | 59 | 1,670 | 4.13 ± 0.03$^c$ (0) | 4.81 ± 0.07$^c$ (0) |
| I.N. | 0.1 | 13 | <20 | 200 | <2.0$^a$ (100) | 4.96 ± 0.14$^c$ (0) |
| | 0.05 | 11 | <20 | 140 | <2.0$^a$ (100) | 4.74 ± 0.21$^c$ (0) |
| | 0.025 | 12 | <20 | 61 | 2.06 ± 0.06$^a$ (92) | 4.85 ± 0.15$^c$ (0) |
| | 0.0125 | 10 | NT | NT | 2.78 ± 0.19$^a$ (30) | 4.36 ± 0.26$^c$ (0) |
| | 0.00625 | 10 | NT | NT | 3.50 ± 0.14$^a$ (0) | 4.30 ± 0.25$^c$ (0) |
| | 0.003125 | 10 | NT | NT | 4.15 ± 0.14$^c$ (0) | 4.86 ± 0.27$^c$ (0) |
| | 0.0015625 | 12 | NT | NT | 4.86 ± 0.12$^c$ (0) | 5.39 ± 0.17$^c$ (0) |

Significance of reduction of viral titer compared to infected animals not treated IVIG:
$^a$p < 0.001
$^b$p < 0.005
$^c$not significant
NT = Not tested Therapeutic effect of IN IVIG not due to neutralization in vitro The possibility that the observed reduction in pulmonary viral titer of animals treated by topical administration of IVIG could be due to neutralization in vitro was evaluated by mixing an equal amount of infected lung tissue from a treated cotton rat (human IVIG administered I.N. at a dose of 0.1 gm/kg 3 days post infection) with infected lung tissue from a cotton rat which had not received IVIG. Mixed homogenates yielded the same amount of virus as lung suspensions from infected cotton rats that had not received IVIG (Table 2). These results indicate that the therapeutic effect observed in IVIG recipients was due to bona fide passive immunity rather than neutralization of virus in vitro following homogenization of lung tissue.

TABLE 2

Therapeutic Effect of IVIG Administered Topically Post Infection Not Attributable to In Vitro Neutralization During Homogenization of Tissues

| RSV-infected lung tissue homogenized | No. of cotton rats | Titer of virus in lungs 4 days after challenge with $10^4$ pfu of RSV (geometric mean, $\log_{10}$ pfu/gm ± S.E.) |
|---|---|---|
| Group A RSV antiserum administered 3 days after virus | 4 | ⎡ 2.76 ± 0.16 ⎤ $a$ |
| Group B Antiserum not administered | 4 | 5.57 ± 0.23 $b$ $a$ |
| Group C Mixture of group A and B tissues | 4 + 4 | ⎣ 5.39 ± 0.13 ⎦ |

$^a$P < 0.001
$^b$Not significant

Topical IVIG therapy does not prolong infection

The possibility was also examined that topical administration of IVIG (0.1 gm/kg) might reduce viral titer on the 4th day post-challenge, but prolong the course of infection. This question was addressed by comparing the titer of RSV in tissues of infected IVIG-treated and control animals at various intervals after treatment (Table 3). In each instance tissues from IVIG-treated animals yielded significantly smaller amounts of virus than tissues from control animals and there was no evidence of a rebound in virus replication.

TABLE 3

Reduction In Level of Pulmonary RSV by Topical Administration of IVIG Is Not Followed By Rebound

| Species of cotton rat | | Pulmonary viral titer ($\log_{10}$ pfu/gm geometric mean ± S.E.) at intervals (days) after IVIG (0.1 gm/kg) was administered I.N. on third day post-infection | | | | | |
|---|---|---|---|---|---|---|---|
| | | 1 | 2 | 3 | 4 | 5 | 7 |
| S. hispidus | IVIG-treated | <2.0 (4)$^a$ | NT | 2.41 ± 0.32 (4) | NT | NT | <2.0 (4) |
| | Untreated | 4.69 ± 0.30 (4) | NT | 4.57 ± 0.16 (4) | NT | NT | <2.0 (4) |
| S. fulviventer | IVIG-treated | 2.61 ± 0.62 (4) | 2.73 ± 0.63 (4) | 2.61 ± 0.42 (4) | <2.0 (4) | <2.0 (4) | <2.0 (5) |
| | Untreated | 5.05 ± 0.13 | 4.96 ± 0.1 | 3.75 ± 0.19 | 3.05 ± 0.36 | <2.0 | <2.0 |

TABLE 3-continued
Reduction In Level of Pulmonary RSV by Topical Administration of IVIG Is Not Followed By Rebound

| Species of cotton rat | Pulmonary viral titer ($\log_{10}$ pfu/gm geometric mean ± S.E.) at intervals (days) after IVIG (0.1 gm/kg) was administered I.N. on third day post-infection | | | | | |
|---|---|---|---|---|---|---|
| | 1 | 2 | 3 | 4 | 5 | 7 |
| | (4) | (4) | (4) | (4) | (4) | (2) |

N.T. = not tested
[a]number of animals

Topical IVIG not associated with increased pulmonary immunopathology

It has been reported that cotton rats previously vaccinated with formalin-inactivated RSV developed enhanced pulmonary pathology, resembling an Arthus reaction, when they were infected with RSV (Prince et al, 1986, *J. Virol.* 57: 721-728). In order to determine whether immunotherapy might initiate immunopathology, lung tissue was harvested from infected cotton rats treated IN with IVIG (0.1 gm/kg) on the third day post-infection and the material examined histologically. Tissues taken 24 and 96 hours after IN administration of IVIG showed no evidence of pathology.

Prophylactic effect of topical IVIG

The possibility that topically-administered IVIG might prove useful during seasonal or situational RSV epidemics for short-term prophylaxis in high-risk situations (such as infants in an intensive-care nursery or patients with congenital heart or pulmonary disease) was examined by administering IVIG IN (0.1 gm/kg) prior to infection and then challenging animals with RSV IN ($10^4$ pfu/animal) at intervals up to seven days later. Four days after challenge, the animals were sacrificed and the titer of pulmonary virus was assayed (Table 4). Although the degree of protection was inversely proportional to the interval between IVIG inoculation and viral challenge, significant protection (p<0.005) was detected as long as 7 days after the immunoglobulin preparation was administered.

TABLE 4
Topically-Administered IVIG Retains Antiviral Activity in the Lungs for Up to Seven Days

| Species of cotton rat | Pulmonary viral titer ($\log_{10}$ pfu/gm geometric mean ± S.E.), 4 days post infection, of cotton rats administered IVIG IN at indicated interval prior to infection ($10^4$ pfu of RSV IN) | | | | | |
|---|---|---|---|---|---|---|
| | Untreated | 1 hour | 1 day | 2 days | 4 days | 7 days |
| S. hispidus | 5.85 ± 0.10 (8)* | <2.0[a] (4) | 3.24 ± 0.43[a] (5) | 4.26 ± 0.43[a] (5) | 4.99 ± 0.06[a] (5) | 5.39 ± 0.09[b] (6) |
| S. fulviventer | 5.83 ± 0.17 (9) | 2.05 ± 0.06[a] (5) | 3.32 ± 0.33[a] (6) | 3.29 ± 0.51[a] (5) | 3.40 ± 0.33[a] (9) | 4.73 ± 0.21[b] (7) |

Significance of reduction of viral titer compared to infected animals not treated with IVIG:
[a]p < 0.001
[b]p < 0.005
*Number of animals Efficacy of Topical administration in owl monkeys The efficacy of topically-administered antibody in owl monkeys is shown in Table 5.

TABLE 5
EFFICACY OF TOPICALLY-ADMINISTERED ANTIBODY IN OWL MONKEYS PREVIOUSLY INFECTED WITH RESPIRATORY SYNCYTIAL VIRUS

| Treatment at Day 5 Post-infection | No. of Animals | Pulmonary viral titers ($\log_{10}$ pfu/m.l., ± S.E.) | |
|---|---|---|---|
| | | Day 5 (Pre-treatment) | Day 7 |
| 400 mg/Kg IgG Intranasally | 10 | 4.26 ± 0.10 | 1.53 ± 0.26* |
| Untreated | 6 | 4.30 ± 0.34 | 3.56 ± 0.09* |

*p 0.001

In summary, the comparative study of the therapeutic efficacy of IVIG administered topically or parenterally described herein shows that whereas 0.025 gm/Kg of IVIG administered topically by the intranasal route effected a $10^{2.2}$-fold reduction in pulmonary viral titer and complete clearance of detectable virus in 92% of animals, 4 gm/Kg of IVIG was required to produce a comparable therapeutic effect when the material was administered parenterally. Thus, the therapeutic effect of IVIG was 160 times greater by the topical route than by parenteral inoculation. For usage in humans, topical therapy can be accomplished by administering the immunoglobulin in such forms as small particle aerosol or the like.

The results further indicate that therapeutic effect of IVIG is permanent because rebound of virus replication in the lungs was not detected. Moreover, as contrasted with previous studies with formalin-treated vaccine, histologic evidence of immunopathology was not seen in the lungs of infected animals which were treated with IVIG topically.

Without being bound to any specific theory, it is postulated that the therapeutic effect of topically administered IVIG appears to be mediated within the lumen of the lung rather than within its parenchyma. The quantity of IVIG present in the serum of topically treated cotton rats which received the smallest dose capable of almost completely clearing RSV from the lungs (i.e., 0.025. gm/Kg) was 61 μg/ml. This level was 200 times lower than the 12,379 μg/ml of IVIG which was present in the serum of animals treated parenterally with the minimum dose that almost completely cleared RSV from the lungs, (i.e., 4 gms/Kg). Thus, the amount of IVIG in the serum of infected cotton rats successfully treated topically with immunoglobulin was substantially below the concentration of IVIG associated with a full therapeutic effect in parenterally treated animals. This implies that IVIG exerts its therapeutic effect within the air passages of the lungs.

The surprising finding to emerge from this study was the duration of activity of topically administered antibodies, wherein a single IN inoculation of IVIG provided significant resistance for seven days. For protecting children or infants, the RSV antibodies are administered by aerosol means or the like to high-risk infants hospitalized during RSV epidemics, no more than about twice a week, thereby substantially reducing the risk of nosocomial infection and disease. A single dose of IVIG, rapidly delivered by small particle aerosol for therapy in serious RSV lower respiratory tract disease in young infants now also becomes possible. It should be noted that compared to the quick results obtained by the topical application as disclosed by the present invention, the currently available therapy for RSV requires the delivery of ribavirin by small particle aerosol device for 12–20 hours a day for at least 3 days.

Clearly, therefore, the present invention opens a new vista for more effective and rapid prevention and treatment of lower respiratory tract viral infection and disease through the topical administration of virus-specific antibodies. A definitive advantage of the new treatment modality disclosed herein is that a material which is already licensed for parenteral use in humans can now also be applied via topical route for better results. The same strategy could be utilized to treat or prevent severe, acute lower respiratory tract disease caused by other important viral respiratory pathogens such as influenza A, influenza B, parainfluenza types 1, 2 and 3, and adenovirus.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of treating respiratory disease caused by respiratory scintial virus (RSV), consisting essentially of administering into the lower respiratory tract of a host suffering from respiratory scintial disease of the lower respiratory tract, a single dose of about 0.025 to about 0.05 g/Kg body weight of purified human gamma globulin suitable for administration by intravenous route and containing respiratory scintial virus-neutralizing antibodies at a titer greater than 1:2000 to produce therapeutic effect against disease caused by RSV.

* * * * *